United States Patent [19]
Storrs et al.

[11] Patent Number: 6,034,224
[45] Date of Patent: Mar. 7, 2000

[54] METHOD FOR SOLUBILIZATION AND NATURATION OF SOMATOTROPINS

[75] Inventors: S. Bradley Storrs, Wildwood; Jacob S. Tou, Ballwin; Jessica Marie Ballinger, Wildwood, all of Mo.

[73] Assignee: Monsanto Company, St. Louis, Mo.

[21] Appl. No.: 09/002,565

[22] Filed: Dec. 31, 1997

Related U.S. Application Data

[60] Provisional application No. 60/034,808, Dec. 31, 1996.

[51] Int. Cl.$^7$ ....................................... C07K 3/00
[52] U.S. Cl. ................... 530/399; 530/412; 530/418; 530/425; 530/426
[58] Field of Search .................................. 530/399, 412, 530/418, 425, 426

[56] References Cited

U.S. PATENT DOCUMENTS

| | | | |
|---|---|---|---|
| 3,985,722 | 10/1976 | Yoshida et al. | 260/112 R |
| 4,443,539 | 4/1984 | Fraser et al. | 435/68 |
| 4,511,503 | 4/1985 | Olson et al. | 260/112 R |
| 4,518,526 | 5/1985 | Olson | 260/112 R |
| 4,652,630 | 3/1987 | Bentle et al. | 530/344 |
| 4,677,196 | 6/1987 | Rausch et al. | 530/412 |
| 4,766,205 | 8/1988 | Ghosh-Dastidar | 530/402 |
| 4,766,224 | 8/1988 | Rausch | 530/412 |
| 4,888,416 | 12/1989 | Janski et al. | 530/399 |
| 4,975,529 | 12/1990 | Frazier et al. | 530/399 |
| 4,977,248 | 12/1990 | Creighton | 530/412 |
| 4,985,544 | 1/1991 | Yokoo et al. | 530/399 |
| 5,023,323 | 6/1991 | Ho | 530/399 |
| 5,109,117 | 4/1992 | Ho | 530/399 |
| 5,182,369 | 1/1993 | Storrs et al. | 530/647 |
| 5,240,834 | 8/1993 | Frankel et al. | 435/71.2 |
| B1 4,652,630 | 11/1992 | Bentle et al. | 530/344 |

FOREIGN PATENT DOCUMENTS

| | | |
|---|---|---|
| 0 103 395 | 3/1984 | European Pat. Off. . |
| 0 192 629 | 8/1986 | European Pat. Off. . |
| 0 218 374 | 4/1987 | European Pat. Off. . |
| 0 226 448 | 6/1987 | European Pat. Off. . |
| 0 263 902 | 4/1988 | European Pat. Off. . |
| 0 295 859 | 12/1988 | European Pat. Off. . |
| 0 312 358 | 4/1989 | European Pat. Off. . |
| 0 229 110 | 5/1992 | European Pat. Off. . |
| WO 87/00204 | 1/1987 | WIPO . |
| WO 87/02985 | 5/1987 | WIPO . |
| WO 93/19776 | 10/1993 | WIPO . |
| WO 95/12385 | 5/1995 | WIPO . |
| WO 95/14037 | 5/1995 | WIPO . |

OTHER PUBLICATIONS

Ajinomoto company brochure, Amino acid based surfactant Amisoft (Dec. 1994).

Goeddel et al., Direct Expression in *Escherichia coli* of a DNA Sequence Coding for Human Growth Hormone. (1979) *Nature* 281:544–48.

Gray et al., Synthesis of Bovine Growth by *Streptomyces lividans*. (1984) *Gene* 32:21–30.

Langley et al., Recombinant–DNA–derived bovine growth hormone from *Escherichia coli* 1. Demonstration that the hormone is expressed in reduced form, and isolation of the hormone in oxidized, native form. (1987) *Eur. J. Biochem.* 163:313–21.

Schoner et al., Role of mRNA Translational Efficient in Bovine Growth Hormone Expression in *Escherichia coli*. (1984) *Proc. Natl. Acad. Sci. U.S.A.* 81:5403–07.

Seeburg et al., Efficient Bacterial Expression of Bovine and Porcine Growth Hormones. (1983) *DNA* 2:37–45.

Ninomiya et al., "Effects of Sodium Acylglutamate in Solid Detergents on Epidirmal Proteins" Caplus # 1974:44522, 1974.

*Primary Examiner*—Michael P. Woodward
*Assistant Examiner*—C. Delacroix-Muirheid
*Attorney, Agent, or Firm*—George R. Beck; Arnold White & Durkee

[57] ABSTRACT

A method for the solubilization and/or naturation of a somatotropin involves contacting a somatotropin with a detergent composition and water under conditions effective to obtain a naturated somatotropin, wherein the detergent composition may be a $C_{10}$, $C_{12}$, $C_{16}$ or $C_{18}$ acyl glutamate, a $C_{10}$, $C_{14}$ or $C_{18}$ alkyl sulfate, an alcohol ethoxy sulfate, lauroyl ethylenediamine-triacetic acid (LEDA), a $C_{10}$ to $C_{18}$ linear alkyl benzene sulfonate, diphenyl disulfonate or an acyl amino acid.

26 Claims, No Drawings

METHOD FOR SOLUBILIZATION AND NATURATION OF SOMATOTROPINS

This application claims the benefit of U.S. provisional application Serial No. 60/034,808, filed Dec. 31, 1996.

BACKGROUND OF THE INVENTION

Somatotropins are growth hormones which were originally discovered in pituitary gland extracts of various animals. Recombinant DNA technology has permitted the expression of somatotropins as heterologous proteins from various host cells. Such recombinant somatotropins, e.g., somatotropins produced in a microorganism such as *E. coli* bacteria that has been transformed using recombinant DNA, are typically produced by the host cell in a precipitated, denatured state having reduced or substantially no bioactivity. The absence of bioactivity is generally attributed to the conformation of the recombinant somatotropin molecule, which lacks the formation of disulfide bonds. Recombinant somatotropins are believed to be produced by the host cell in substantially reduced form (without disulfide linkages) due to the relatively high redox potential of host cells such as the *E. coli* cell. Most recombinant somatotropins, such as bovine (bST) and porcine somatotropin (pST), are packaged in the host cell as inclusion bodies, also referred to as refractile bodies, which are cytoplasmic aggregates containing the recombinant somatotropin and oligomers thereof.

In order to recover the recombinant somatotropin in a bioactive state, the somatotropin, e.g., in the form of inclusion bodies, is preferably but not necessarily isolated from the host cell, after which the somatotropin may be solubilized to form somatotropin monomers, which may then be naturated into a bioactive conformation. The naturated somatotropin may then be further purified to remove impurities such as other somatotropin species, e.g., oligomers such as dimers, and host cell proteins, for example, by ion exchange to precipitate the impurities (e.g., as described in U.S. Pat. No. 5,182,369, which is incorporated herein by reference) or other suitable techniques.

For example, Bentle et al., U.S. Pat. No. 4,652,630, which is incorporated herein by reference, refers to a method for solubilization and naturation of somatotropin protein from inclusion bodies using an aqueous solution of urea to solubilize the inclusion bodies containing the recombinant somatotropin. Bentle et al. reports using urea solutions having concentrations ranging from 2.5 to 7.5 M and a pH between about 9 and 12 for the solubilization step. Once solubilized, the somatotropin protein can be naturated according to the Bentle et al. method at an alkaline pH.

Other methods have used a detergent to solubilize and naturate a somatotropin. For example, European Patent Specification publication nos. 229,110 and 263,902 (The Upjohn Co.), which are incorporated herein by reference, disclose a method for converting an insoluble form of somatotropin from a transformed microorganism to the native disulphide bond conformation by solubilizing and oxidizing the somatotropin in the presence of a detergent. That method uses a detergent of sodium dodecylsulfate (SDS) or a detergent of the formula:

$$CH_3—(CH_2)_n—CO—NR_1—CHR_2—COOH,$$

wherein n is 8 through 20 inclusive; $R_1$ is methyl or ethyl; and $R_2$ is hydrogen, ethyl, methyl, n-propyl or isopropyl. These specifications further disclose a particular method for solubilizing recombinant bST using an aqueous solution of N-lauroyl methyl glycine, which is represented by the formula:

$$CH_3—(CH_2)_{10}—CO—NR_1—CHR_2—COOH,$$

in a sodium borate buffer at 0.1 to 0.5 M and a pH of 8 to 10.5. After solubilization and naturation, European Patent Specification publication nos. 229,110 and 263,902 state that the detergent is removed by an anion exchange resin.

Other publications also disclose methods for the solubilization and naturation of recombinant somatotropins using various detergent and non-detergent compounds including U.S. Pat. Nos. 4,677,196 and 4,766,224, which also use SDS; U.S. Pat. No. 5,023,323, which uses SDS in combination with a chaotropic agent such as urea or guanidine hydrochloride; U.S. Pat. No. 5,240,834, which uses sarkosyl (N-lauroyl sarcosine), and U.S. Pat. No. 4,975,529, which uses 2-amino-2-methyl-1-propanol. Each of these patents are incorporated herein by reference. Although SDS has been reported in several references for use in somatotropin solubilization and naturation methods, it is further acknowledged that SDS binds relatively tightly to the naturated somatotropin, thus making its complete removal from the somatotropin solution difficult.

There is a need in the art for more economical and efficient methods to obtain recombinant somatotropins with high yield and purity. In particular, there is a need for methods for the solubilization and naturation of recombinant somatotropin proteins to obtain the somatotropin molecules in a bioactive state, preferably using a low amount of detergent that is readily biodegradable. There is a further need for such methods that use a detergent that is easily removed from the naturated somatotropin.

SUMMARY OF THE INVENTION

This invention generally relates to methods for producing biologically active recombinant somatotropins. More particularly, this invention relates to methods for the solubilization and naturation of recombinant somatotropins comprising contacting a somatotropin with a detergent composition and water under conditions effective to obtain a naturated somatotropin, wherein the detergent composition comprises a $C_{10}$ to $C_{18}$ acyl glutamate, a $C_{10}$, $C_{14}$ or $C_{18}$ alkyl sulfate, an alcohol ethoxy sulfate, lauroyl ethylenediaminetriacetic acid (LEDA), a $C_{10}$ to $C_{18}$ linear alkyl benzene sulfonate, diphenyl disulfonate or an acyl amino acid of formula (I) or formula (II):

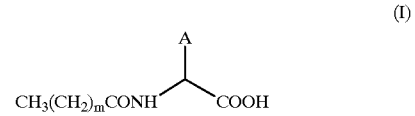
(I)

wherein A is $CH_2CH_2CO_2H$, $CH_2CH_2SCH_3$, $CH_2CO_2H$, $CH_2CONH_2$, $CH_2CH_2CH_2CONH_2$, $CH(CH_3)_2$, $CH_2CH(CH_3)_2$, $CH(CH_3)CH_2CH_3$, $CH_2C_6H_5$, $CH_2C_6H_4OH$ or $CH_2OH$ and m is an integer from 8 to 16;

$$CH_3(CH_2)_mCONH(CH_2)_nCO_2H \qquad (II)$$

wherein n is an integer from 1 to 5 and m is an integer from 8 to 16.

In a further preferred embodiment, the invention is directed to a method for the solubilization and naturation of a recombinant somatotropin using low amounts of biodegradable detergents that are easily removed from the naturated somatotropin by diafiltration, such as a $C_{10}$ or $C_{12}$ acyl glutamate, N-lauroyl sarcosine, N-decylsulfate (NDS) or lauroyl ethylenediaminetriacetic acid (LEDA).

DESCRIPTION OF ILLUSTRATIVE EMBODIMENTS

The present invention is directed to a method for the naturation of a somatotropin comprising the step of contacting a somatotropin with a detergent composition and water under conditions effective to obtain a naturated somatotropin, wherein the detergent composition comprises a $C_{10}$ to $C_{18}$ acyl glutamate, a $C_{10}$, $C_{14}$ or $C_{18}$ alkyl sulfate, an alcohol ethoxy sulfate, lauroyl ethylenediaminetriacetic acid (LEDA), a $C_{10}$ to $C_{18}$ linear alkyl benzene sulfonate, diphenyl disulfonate or an acyl amino acid of the formula (I) or (II):

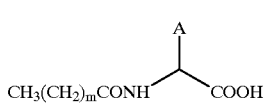

(I)

wherein A is $CH_2CH_2CO_2H$, $CH_2CH_2SCH_3$, $CH_2CO_2H$, $CH_2CONH_2$, $CH_2CH_2CONH_2$, $CH(CH_3)_2$, $CH_2CH(CH_3)_2$, $CH(CH_3)CH_2CH_3$, $CH_2C_6H_5$, $CH_2C_6H_4OH$, or $CH_2OH$ and m is an integer from 8 to 16;

(II)

wherein n is an integer from 1 to 5 and m is an integer from 8 to 16. The detergent composition can also comprise an N-alkylated derivative of formula (I) or (II).

The invention is further directed to a method for the solubilization and naturation of a somatotropin comprising the steps of contacting a somatotropin with a detergent composition and water under conditions effective to solubilize the somatotropin, and subsequently adjusting the pH of the resulting somatotropin solution to naturate the somatotropin, wherein the detergent composition comprises a $C_{10}$ to $C_{18}$ acyl glutamate, a $C_{10}$, $C_{14}$ or $C_{18}$ alkyl sulfate, an alcohol ethoxy sulfate, lauroyl ethylenediaminetriacetic acid (LEDA), a $C_{10}$ to $C_{18}$ linear alkyl benzene sulfonate, diphenyl disulfonate or an acyl amino acid of the formula (I) or (II):

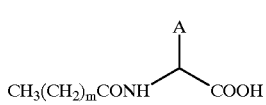

(I)

wherein A is $CH_2CH_2CO_2H$, $CH_2CH_2SCH_3$, $CH_2CO_2H$, $CH_2CONH_2$, $CH_2CH_2CONH_2$, $CH(CH_3)_2$, $CH_2CH(CH_3)_2$, $CH(CH_3)CH_2CH_3$, $CH_2C_6H_5$, $CH_2C_6H_4OH$, or $CH_2OH$ and m is an integer from 8 to 16;

(II)

wherein n is an integer from 1 to 5 and m is an integer from 8 to 16. The detergent composition can also comprise an N-alkylated derivative of formula (I) or (II).

For purposes of the present invention, the following terms should be considered to have the definitions listed below.

The term "somatotropin" includes mammalian somatotropins, such as bovine, porcine, human, ovine, equine, canine and feline somatotropin, and others such as avian somatotropin. Somatotropins, for purposes of this specification, includes somatotropin proteins having naturally-occurring sequences, analogs and homologs of the naturally-occurring protein having somatotropin-like bioactivity, i.e., they bind to somatotropin receptors in the animal with affinity great enough to enhance juvenile growth rate, lactation and/or feed efficiency. Somatotropins also include variants of the naturally-occurring somatotropin that have been lengthened, shortened, substituted and/or fused to another protein, provided that such variants are subject to solubilization and/or naturation according to the inventive process.

"Recombinant" proteins, also referred to as heterologous proteins, are proteins which are normally not produced by the host cell. Recombinant DNA technology has permitted the expression of relatively large amounts of heterologous proteins from transformed host cells. For example, expression of recombinant somatotropins from a variety of animals by transformed microorganisms is known. Examples include Goeddel, et al., "Direct Expression in *Escherichia coli* of a DNA Sequence Coding for Human Growth Hormone," *Nature* 281:544–48 (1979) and Seeburg, et al., "Efficient Bacterial Expression of Bovine and Porcine Growth Hormones," *DNA* 2:37–45 (1983). The production of somatotropins in transformed microorganisms can be achieved by a variety of recombinant genetic plasmids. Examples include those described in United Kingdom Patent Application GB 20732445A; and Schoner et al., "Role of mRNA Translational Efficiency in Bovine Growth Hormone Expression in *Escherichia coli*," *PNAS USA* 81:5403–07 (1984). Analogs of bST are also known, for example, as disclosed in European Patent Application No. 103,395. The production of bST in transformed microorganisms other than *E. coli* has been reported by Gray, et al., "Synthesis of Bovine Growth Hormone by *Streptomyces lividans*," *Gene* 32:21–30 (1984), and in U.S. Pat. No. 4,443,539 for yeast.

"Inclusion bodies," also referred to as "refractile bodies," are the cytoplasmic aggregates and oligomers containing the recombinant somatotropin to be recovered.

A "host cell" is a microbial cell such as bacteria, yeast or other suitable cells such as animal and plant cells that has been transformed to express the recombinant somatotropin. An exemplary host cell is *E. coli* K12 (strain W3110/pBGH-1) which has been transformed to permit expression of bovine somatotropin.

"Naturation" involves the formation of correct disulfide bonds such that the somatotropin protein is biologically active upon completion of the naturation step or after further purification. "Folding" refers to the return of the overall conformational shape of the protein sufficient to permit proper oxidation. "Oxidation" refers to the formation of the intramolecular disulfide bonds generally required for a biologically active conformation, preferably the native biologically active conformation.

"Biological activity" means that the subject somatotropin is capable of effecting its intended in vivo physiological response. The biological activity can be determined in the absence of in vivo testing in the particular species by carrying out suitable bioassays. A suitable bioassay for the somatotropins is the "rat weight gain bioassay." In this bioassay, the bioactivity of somatotropin preparations are assessed relative to a known preparation (i.e., extracted native somatotropin) by relating the amount of weight gain of hypophysectomized rats to varying amounts of administered preparation.

The methods for solubilization and naturation of somatotropins according to the invention may be applied to any type of recombinant somatotropin, particularly bovine somatotropin (bST), porcine somatotropin (pST) and human somatotropin (hST). The transformation, culturing and fermenting of host cells to produce recombinant somatotropin may be performed by conventional methods. The recombinant somatotropin, generally in the form of inclusion bodies, may also be recovered from the host cell culture by conventional techniques that disrupt the cell so as to release the inclusion bodies, and thereupon the inclusion bodies may be collected as a pellet by differential centrifugation.

The detergent composition to be used in the inventive method generally contains a detergent or combination of detergents that promotes the solubilization of somatotropin obtained from the host cell and/or naturates the somatotropin molecules. More preferably, the detergent used in the inventive methods is also easily removed from the somatotropin solution upon completion of the naturation step. The detergent composition to be used in the inventive methods may comprise one or more compounds selected from a $C_{10}$ to $C_{18}$ acyl glutamate, a $C_{10}$, $C_{14}$ or C18 alkyl sulfate, an alcohol ethoxy sulfate, lauroyl ethylenediaminetriacetic acid (LEDA), a $C_{10}$ to $C_{18}$ linear alkyl benzene sulfonate, diphenyl disulfonate or an acyl amino acid of the formula (I) or (II):

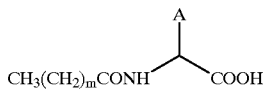
(I)

wherein A is $CH_2CH_2CO_2H$, $CH_2CH_2SCH_3$, $CH_2CO_2H$, $CH_2CONH_2$, $CH_2CH_2CONH_2$, $CH(CH_3)_2$, $CH_2CH(CH_3)_2$, $CH(CH_3)CH_2CH_3$, $CH_2C_6H_5$, $CH_2C_6H_4OH$, or $CH_2OH$ and m is an integer from 8 to 16;

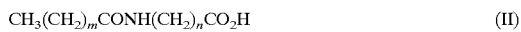
(II)

wherein n is an integer from 1 to 5 and m is an integer from 8 to 16. The detergent composition can also comprise an N-alkylated derivative of formula (I) or (II).

In a preferred embodiment, the detergent is a $C_{10}$ to $C_{18}$ acyl glutamate or a salt thereof, and more preferably a $C_{10}$, $C_{12}$, $C_{16}$ or $C_{18}$ acyl glutamate or a salt thereof. For example, the acyl radical may be cocoyl, lauroyl, stearoyl or a mixture thereof. In a preferred embodiment, the acyl glutamate is an acyl glutamate salt of triethanolamine, sodium or potassium. More preferably, the acyl glutamate is sodium lauroyl glutamate (available as AMISOFT LS-11 or AMISOFT LS-11(F) from Ajinomoto), sodium cocoyl glutamate (available as AMISOFT CS-11 or AMISOFT CS-11(F) from Ajinomoto), TEA cocoyl glutamate (available as AMISOFT CT-12 or AMISOFT CT-12S from Ajinomoto), TEA lauroyl glutamate (available as AMISOFT LT-12 from Ajinomoto), sodium hydrogenated tallowyl glutamate (available as AMISOFT HS-11 or AMISOFT HS-11(F) from Ajinomoto), sodium hydrogenated tallowyl glutamate with sodium cocoyl glutamate (available as AMISOFT GS-11 or AMISOFT GS-11(F) from Ajinomoto), disodium hydrogenated tallowyl glutamate (available as AMISOFT HS-21 from Ajinomoto), potassium cocoyl glutamate (available as AMISOFT CK-11 or AMISOFT CK-11(F) from Ajinomoto), cocoyl glutamic acid (available as AMISOFT CA from Ajinomoto) or hydrogenated tallowyl glutamic acid (stearoyl glutamic acid) (available as AMISOFT HA from Ajinomoto). More preferably, the detergent composition comprises an acyl glutamate of sodium lauroyl glutamate, sodium hydrogenated tallowyl glutamate, sodium cocoyl glutamate, disodium cocoyl glutamate or a combination thereof. Most preferably, the detergent composition comprises a $C_{10}$ or $C_{12}$ acyl glutamate, and in particular, sodium lauroyl glutamate.

The detergent can also be an N-alkylated derivative of formula (I) or (II), such as acyl N-methyl glutamate, acyl N-methyl aspartate or an N-methyl derivative of Sarkosyl or Amilite.

Acyl glutamate can be added to the subject somatotropin mixture, for example, as a powder or in solution form. For example, acyl glutamate can be prepared as a 10% stock solution having a pH of about 6.9–7.0 by adding 0.84 L $H_2O$, 61 mL 10% NaOH, and 100 g of acyl glutamate powder. During the solubilization and naturation steps, acyl glutamate is preferably present in the overall mixture at a concentration in the range of about 0.2 to about 5% weight based on the total naturation mixture, and more preferably about 0.3 to about 3%.

The use of acyl glutamates in the detergent composition in the inventive methods provides a number of economical and environmental advantages, as acyl glutamates are generally available at low cost and high purity and are readily biodegradable. The use of certain acyl glutamates also adds to the overall economics of the inventive methods as they are easily separated from the mixture of naturated somatotropin, particularly by diafiltration, thereby reducing equipment and operation costs.

Alternatively, the detergent composition used in the inventive methods comprises a $C_{10}$, $C_{14}$ or $C_{18}$ alkyl sulfate, such as NDS; an alcohol ethoxy sulfate, such as $C_{12}H_{25}O(CH_2CH_2O)SO_3Na$ or $C_{12}H_{25}O(CH_2CH_2O)_3SO_3Na$ (available from Stepan Co. as Steol™ CS-130, CS-330 or CS-430) or $C_{14}H_{29}O(CH_2CH_2O)_3SO_3Na$ (available from Henkel Corp. as Standapol™ ES-40); LEDA (available from Hampshire Corp. as Hampshire LEDA); a $C_{10}$ to $C_{18}$ linear alkyl benzene sulfonate, such as a linear dodecylbenzene sulfonate; diphenyl disulfonate or an acyl amino acid of the formula (1) or (II):

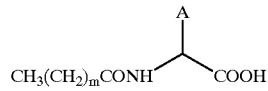
(I)

wherein A is $CH_2CH_2CO_2H$, $CH_2CH_2SCH_3$, $CH_2CO_2H$, $CH_2CONH_2$, $CH_2CH_2CONH_2$, $CH(CH_3)_2$, $CH_2CH(CH_3)_2$, $CH(CH_3)CH_2CH_3$, $CH_2C_6H_5$, $CH_2C_6H_4OH$, or $CH_2OH$ and m is an integer from 8 to 16;

(II)

wherein n is an integer from 1 to 5 and m is an integer from 8 to 16.

The solubilization and naturation steps may be conducted at the same volume and detergent concentration. Alternatively, the solubilization step may proceed at less than the final naturation volume as solubilization of the subject protein may be facilitated at higher detergent concentrations. The somatotropin solution may then be diluted to obtain the final naturation volume. For example, the somatotropin may be solubilized in a detergent solution having half of the final naturation volume, after which an amount of water or buffer is added to obtain the full naturation volume.

The pH of the solubilization step is preferably in the range of about 9 to about 13, and more preferably in the range of about 10 to about 12. The pH of the naturation solution is preferably in the range of about 8 to about 12, more preferably about 9 to about 11 and most preferably about 9.5 to about 10.5.

The naturated somatotropin obtained by the inventive methods is preferably obtained in at least about 80% yield, for example, in a yield of about 85% to 95%, wherein the yield is defined as [naturated somatotropin monomer]/[total reduced somatotropin monomer].

A catalyst, such as cystine or cysteine, may be optionally added to the somatotropin composition of the naturation step to increase the rate of formation of the disulfide bonds.

The detergent composition used for solubilization and/or naturation of the somatotropin is preferably removed from the somatotropin solution after the naturation step to avoid interference with downstream purification steps. The detergent composition may be removed by a variety of methods including ion-exchange, dialysis or combinations of those techniques. In a preferred embodiment, the detergent is removed from the naturated somatotropin composition by diafiltration. In a further preferred embodiment, the diafiltration is conducted with a cellulose membrane. Removal of detergents such as $C_{10}$ and $C_{12}$ acyl glutamates, N-lauroyl sarcosine, NDS or LEDA by diafiltration is a significant processing advantage as certain detergents are removed from the somatotropin mixture with a significantly lower number of turnover volumes than known processes. When some detergents are removed by diafiltration alone, they may require in excess of 80 volumes of diafiltration buffer. This large volume is a disadvantage in processing because of the size of the diafiltration equipment required. In contrast, $C_{10}$ and $C_{12}$ acyl glutamates, N-lauroyl sarcosine, NDS, and LEDA have been found to be easily removed with preferably fewer than 30 turnover volumes. $C_{10}$ and $C_{12}$ acyl glutamates are particularly amenable to removal by diafiltration and are more preferably removed in about 10 to 20 turnover volumes.

Precipitation of impurities and purification of the naturated somatotropin composition having the detergent composition substantially removed may be carried out by conventional methods. For example, Storrs et al., U.S. Pat. No. 5,182,369 and Bentle et al., U.S. Pat. No. 4,652,630, which are incorporated herein by reference, refer to methods for purifying and recovering biologically active somatotropin monomers from solution following the solubilization and naturation of inclusion bodies of host cells produced by recombinant DNA methodology.

The methods of the present invention are preferably part of an overall technique for producing a somatotropin product that is suitable for parenteral application to target animals.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Four varieties of acyl glutamate and lauroyl ethylenediaminetriacetic acid (LEDA) were tested and shown to be highly efficient at solubilizing bovine somatotropin (bST) inclusion bodies and allowing the correct maturation of the bST molecules (Examples 1–3). Examples are also provided for the solubilization and maturation of porcine somatotropin (pST) (Examples 3–4).

Example 1

Solubilization of bST Inclusion Bodies

An aqueous slurry of bST inclusion bodies was assayed and determined to contain 45 g bST/L. The bST used was the N-methionyl derivative of bST otherwise having the native amino acid sequence beginning with phenylalanine. These solubilization experiments were conducted at room temperature, a solution pH of 11.5 and at 20 g bST/L. The solubilization was performed at one half of the maturation volume, i.e., if the naturation was to be carried out in a 1% detergent and at 10 g bST/L, the solubilization was carried out in a 2% detergent and at 20 g bST/L. The volume was doubled after the solubilization to start the naturation.

Water, detergent and NaOH were combined. A sufficient amount of the base was added such that after the inclusion bodies were added and dissolved, the pH was 11.5, as determined in a preliminary experiment. The mixture of water, detergent and base was stirred as the inclusion bodies were added, after which stirring was continued for 30 minutes.

Example 2

Naturation of bST

The naturation step was also conducted at room temperature. Following the solubilization step, the pH was adjusted to 9.5 by adding HCl, which also served to nearly double the volume. Water was then added to bring the solution to its final volume. Cystine was then added to achieve a final concentration of 1 mM cystine. The mixture was then stirred overnight to complete the naturation process.

Examples 1 and 2 were conducted for four different acyl glutamate detergent compositions, sodium lauroyl glutamate, sodium hydrogenated tallowyl glutamate with sodium cocoyl glutamate, sodium hydrogenated tallowyl glutamate and disodium cocoyl glutamate, and LEDA as well as a comparative detergent of sodium lauroyl sarcosinate. Tables 1 and 2 below summarize the naturation efficiencies a various pH conditions and detergent concentrations.

TABLE 1

Naturation Efficiencies (%) for Solubilization pH of 11.5 and Naturation pH of 9.5

| DETERGENT | Detergent Concentrations | | | | | | | |
|---|---|---|---|---|---|---|---|---|
|  | 0.05 | 0.10 | 0.25 | 0.50 | 1.00 | 1.50 | 2.00 | 2.50 |
| Sodium lauroyl glutamate | — | — | — | — | — | 90 | — | — |
| Sodium hydrogenated tallowyl glutamate + sodium cocoyl glutamate | — | — | — | 93 | 94 | 75 | 37 | 23 |
| Sodium hydrogenated tallowyl glutamate | — | 54 | 76 | 95 | 88 | 57 | 25 | 15 |
| Disodium cocoyl glutamate | — | — | — | 63 | 81 | 88 | 69 | 32 |
| Lauroyl ethylenediaminetri acetic acid | — | — | — | — | — | — | 67 | 83 |
| Sodium lauroyl sarcosinate* | 28 | 37 | 43 | 89 | 65 | 50 | 45 | 45 |

*Comparative example

TABLE 2

Naturation Efficiencies (%) at Various Naturation pH Values

| DETERGENT | Refold pH | | | |
|---|---|---|---|---|
| | 8.5 | 9.5 | 10.5 | 11.5 |
| Sodium lauroyl glutamate | 77 | 90 | 85 | 79 |
| Sodium hydrogenated tallowyl glutamate | 84 | 95 | 97 | 82 |
| Disodium cocoyl glutamate | 71 | 88 | 88 | 76 |
| Lauroyl ethylenediamine triacetic acid | 68 | 83 | 76 | 69 |
| Sodium lauroyl sarcosinate.* | 81 | 89 | 81 | 67 |

*Comparative example

Example 3

Solubilization and Naturation of pST

PST was solubilized at half of the ultimate naturation volume in 3% lauroyl acylglutamate, 20 g/L pST, pH 11 to 11.5 at room temperature. The pST used was that having the native amino acid sequence beginning with phenylalanine and having an additional alanine at the amino terminus. Following solubilization, 15 to 30 min., the pH was adjusted with HCl, diluted with deionized water to final naturation volume, followed by addition of the cystine catalyst. Final naturation conditions were 10 g/L pST, 1.5% acylglutamate, 1 mM cystine, pH 9.5, at room temperature. The naturation was completed within a few hours.

Example 4

Removal of Acyl Glutamate Detergent From Naturated pST

The lauroyl acyl glutamate detergent used in the naturation step was removed by diafiltration prior to pH precipitation to remove impurities. The acylglutamate was adequately removed with 15 to 20 turnover volumes of cold diafiltration buffer of 1 mM NaOH in deionized water.

While the methods of this invention have been described in terms of preferred embodiments, it will be apparent to those of skill in the art that variations may be applied to the method described herein without departing from the concept, spirit and scope of the invention. All such similar substitutes and modifications apparent to those skilled in the art are deemed to be within the spirit, scope and concept of the invention.

What is claimed is:

1. A method for the naturation of a somatotropin comprising:
   contacting a somatotropin with a detergent composition and water under conditions effective to obtain a naturated somatotropin, wherein the detergent composition comprises a $C_{10}$, $C_{12}$, $C_{16}$ or $C_{18}$ acyl glutamate.

2. The method of claim 1, wherein the somatotropin is bovine, porcine or human somatotropin.

3. The method of claim 1, wherein the naturated somatotropin yield is at least about 80%.

4. The method of claim 1, wherein the acyl glutamate is a lauroyl glutamate, a cocoyl glutamate, a tallowyl glutamate or a salt thereof.

5. The method of claim 1, wherein the acyl glutamate is sodium lauroyl glutamate, sodium cocoyl glutamate, TEA cocoyl glutamate, TEA lauroyl glutamate, sodium hydrogenated tallowyl glutamate, sodium hydrogenated tallowyl glutamate with sodium cocoyl glutamate, disodium hydrogenated tallowyl glutamate, potassium cocoyl glutamate, cocoyl glutamic acid or hydrogenated tallowyl glutamic acid.

6. The method of claim 5, wherein the acyl glutamate is sodium lauroyl glutamate, sodium hydrogenated tallowyl glutamate, sodium cocoyl glutamate, sodium hydrogenated tallowyl glutamate with sodium cocoyl glutamate, or disodium cocoyl glutamate.

7. The method of claim 1, wherein the detergent composition comprises a $C_{10}$ or $C_{12}$ acyl glutamate and the method further comprises separating the acyl glutamate from the naturated somatotropin by diafiltration.

8. The method of claim 7, wherein the diafiltration uses fewer than 30 turnover volumes to remove substantially all of the acyl glutamate from the somatotropin.

9. The method of claim 1, wherein the conditions include a pH in the range of about 8 to about 12.

10. The method of claim 9, wherein the pH is in the range of about 9.5 to about 10.5.

11. The method of claim 1, wherein the conditions include a detergent concentration in the range of about 0.2 to about 5% by weight.

12. A method for solubilization and naturation of a somatotropin comprising:
   contacting a somatotropin with a detergent composition and water under conditions effective to solubilize the somatotropin, and
   adjusting the pH of the resulting somatotropin solution to naturate the somatotropin,
   wherein the detergent composition comprises a $C_{10}$, $C_{12}$, $C_{16}$ or $C_{18}$ acyl glutamate.

13. The method of claim 12, wherein the somatotropin is bovine, porcine or human somatotropin.

14. The method of claim 12, wherein the naturated somatotropin yield is at least about 80%.

15. The method of claim 12, wherein the acyl glutamate is a lauroyl glutamate, a cocoyl glutamate, a tallowyl glutamate or a salt thereof.

16. The method of claim 15, wherein the acyl glutamate is sodium lauroyl glutamate, sodium cocoyl glutamate, TEA cocoyl glutamate, TEA lauroyl glutamate, sodium hydrogenated tallowyl glutamate, sodium hydrogenated tallowyl glutamate with sodium cocoyl glutamate, disodium hydrogenated tallowyl glutamate, potassium cocoyl glutamate, cocoyl glutamic acid or hydrogenated tallowyl glutamic acid.

17. The method of claim 16, wherein the acyl glutamate is sodium lauroyl glutamate, sodium hydrogenated tallowyl glutamate, sodium cocoyl glutamate, sodium hydrogenated tallowyl glutamate with sodium cocoyl glutamate or disodium cocoyl glutamate.

18. The method of claim 12, further comprising separating the acyl glutamate from the naturated somatotropin by diafiltration.

19. The method of claim 18, wherein the diafiltration uses fewer than 30 turnover volumes to remove substantially all of the acyl glutamate from the somatotropin.

20. The method of claim 12, wherein the conditions include a pH in the range of about 9 to about 13.

21. The method of claim 12, wherein the conditions include a pH in the range of about 8 to about 12.

22. The method of claim 21, wherein the pH is in the range of about 9.5 to about 10.5.

23. The method of claim 12, wherein the conditions include a detergent concentration in the range of about 0.2 to about 5% by weight.

24. A method for obtaining bioactive somatotropin comprising:
  contacting a somatotropin with a detergent composition and water under conditions effective to solubilize the somatotropin,
  adjusting the pH of the somatotropin solution to naturate the somatotropin, and
  removing the detergent composition from the naturated somatotropin by diafiltration,
wherein the detergent composition comprises a $C_{10}$ or $C_{12}$ acyl glutamate.

25. The method of claim 24, wherein the diafiltration step uses fewer than 30 turnover volumes to remove substantially all of the detergent from the somatotropin.

26. The method of claim 25, wherein the detergent comprises a $C_{12}$ acyl glutamate and the diafiltration step uses from 10 to 20 turnover volumes to remove substantially all of the detergent from the somatotropin.

* * * * *